United States Patent
Hiejima

(10) Patent No.: US 7,914,494 B2
(45) Date of Patent: Mar. 29, 2011

(54) INDWELLING CATHETER

(75) Inventor: Katsuhiro Hiejima, Osaka (JP)

(73) Assignee: Nipro Corporation, Osaka (JP)

( * ) Notice: Subject to any disclaimer, the term of this patent is extended or adjusted under 35 U.S.C. 154(b) by 66 days.

(21) Appl. No.: 11/905,047

(22) Filed: Sep. 27, 2007

(65) Prior Publication Data
US 2008/0027389 A1 Jan. 31, 2008

Related U.S. Application Data

(62) Division of application No. 10/773,409, filed on Feb. 9, 2004, now Pat. No. 7,347,839.

(30) Foreign Application Priority Data

Feb. 12, 2003 (JP) .................................. 2003-33635
Feb. 12, 2003 (JP) .................................. 2003-33636

(51) Int. Cl.
*A61M 5/178* (2006.01)
(52) U.S. Cl. .................................. 604/167.04; 604/533
(58) Field of Classification Search ............. 604/167.04, 604/533
See application file for complete search history.

(56) References Cited

U.S. PATENT DOCUMENTS

| | | | |
|---|---|---|---|
| 4,512,766 A | 4/1985 | Vailancourt | 604/169 |
| 4,874,377 A * | 10/1989 | Newgard et al. | 604/167.02 |
| 4,935,010 A * | 6/1990 | Cox et al. | 604/122 |
| 5,059,186 A * | 10/1991 | Yamamoto et al. | 604/537 |
| 5,322,518 A | 6/1994 | Schneider et al. | 604/247 |
| 5,330,435 A | 7/1994 | Vaillancourt | 604/167 |
| 5,405,323 A * | 4/1995 | Rogers et al. | 604/508 |
| 5,507,732 A | 4/1996 | McClure et al. | 604/280 |
| 5,520,666 A | 5/1996 | Choudhury et al. | 604/283 |
| 6,699,221 B2 * | 3/2004 | Vaillancourt | 604/167.01 |
| 7,736,339 B2 * | 6/2010 | Woehr et al. | 604/164.08 |
| 2002/0016611 A1 * | 2/2002 | Cragg et al. | 606/213 |
| 2002/0128604 A1 * | 9/2002 | Nakajima | 604/164.01 |

FOREIGN PATENT DOCUMENTS

| | | |
|---|---|---|
| EP | 0 343 953 A1 | 11/1989 |
| EP | 1 240 916 A1 | 9/2002 |
| JP | 2002-528038 A | 8/2002 |
| JP | 2002-263197 A | 9/2002 |

* cited by examiner

*Primary Examiner* — Nicholas D Lucchesi
*Assistant Examiner* — Gerald Landry, II
(74) *Attorney, Agent, or Firm* — Kubovcik & Kubovcik

(57) ABSTRACT

An indwelling catheter comprises a tube, a female connector and an elastically deformable hemostasis valve which can be pressed by a male connector. An opening taper portion tapered forwardly is formed in a longitudinal intermediate portion of an inner circumferential surface of the female connector. The elastically deformable hemostasis valve is provided longitudinally slidably in the opening taper portion of the female connector and an inside portion extending rearwardly from the opening taper portion. The hemostasis valve includes; a body having a hollow form opened at its front and rear ends or a tubular portion fitted over the connecting portion from a rearward direction; and an openable/closable portion being opened by elastic deformation of the body or the tubular portion.

12 Claims, 8 Drawing Sheets

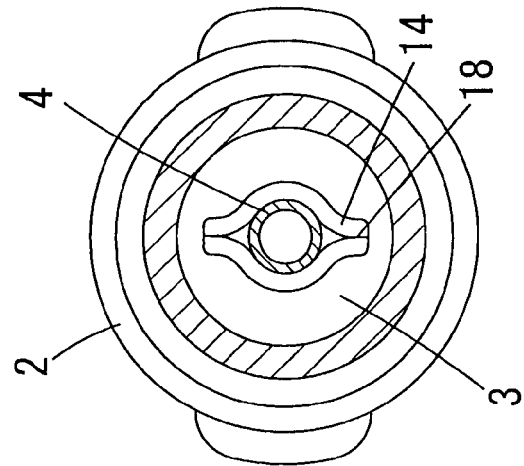
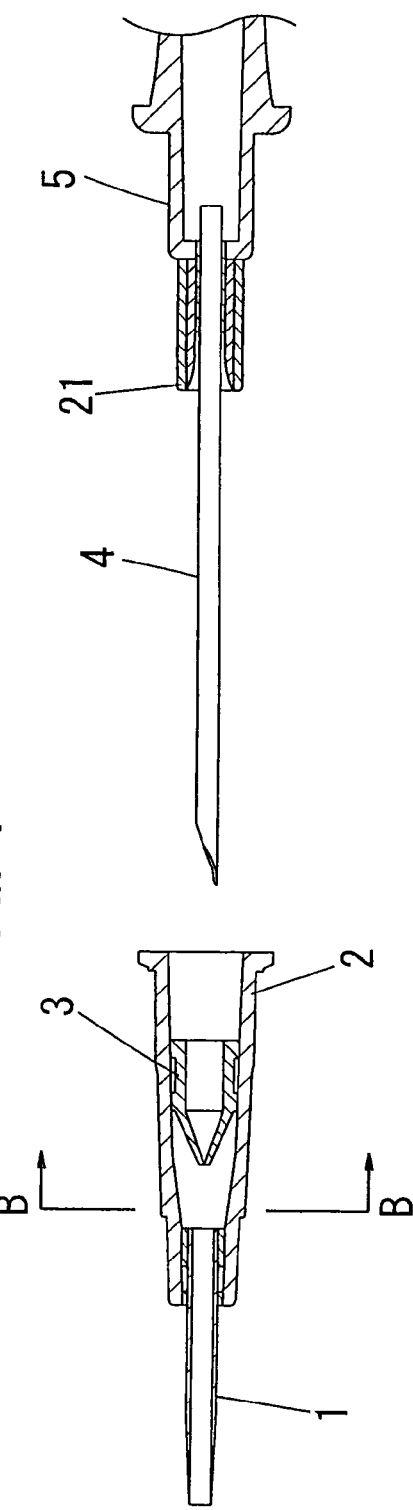

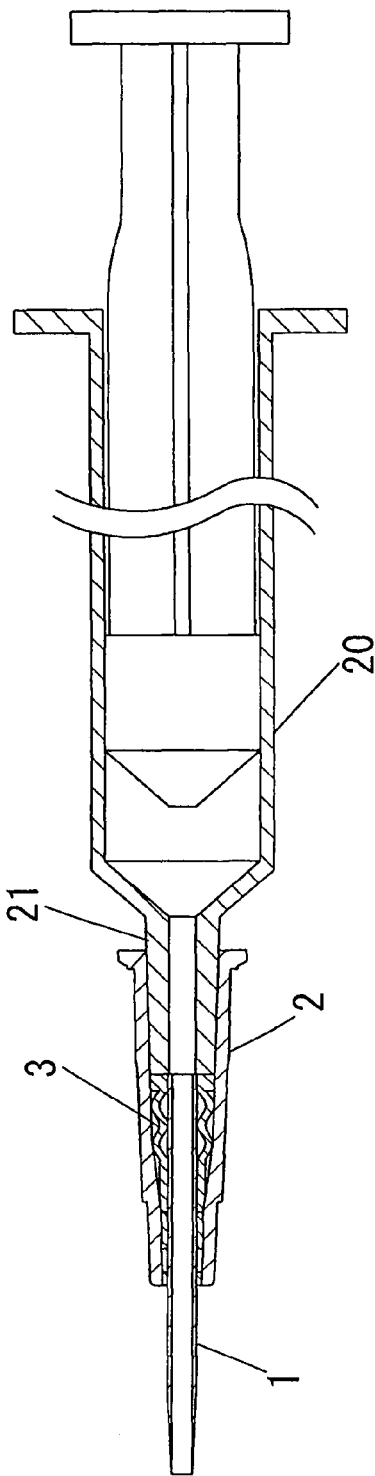
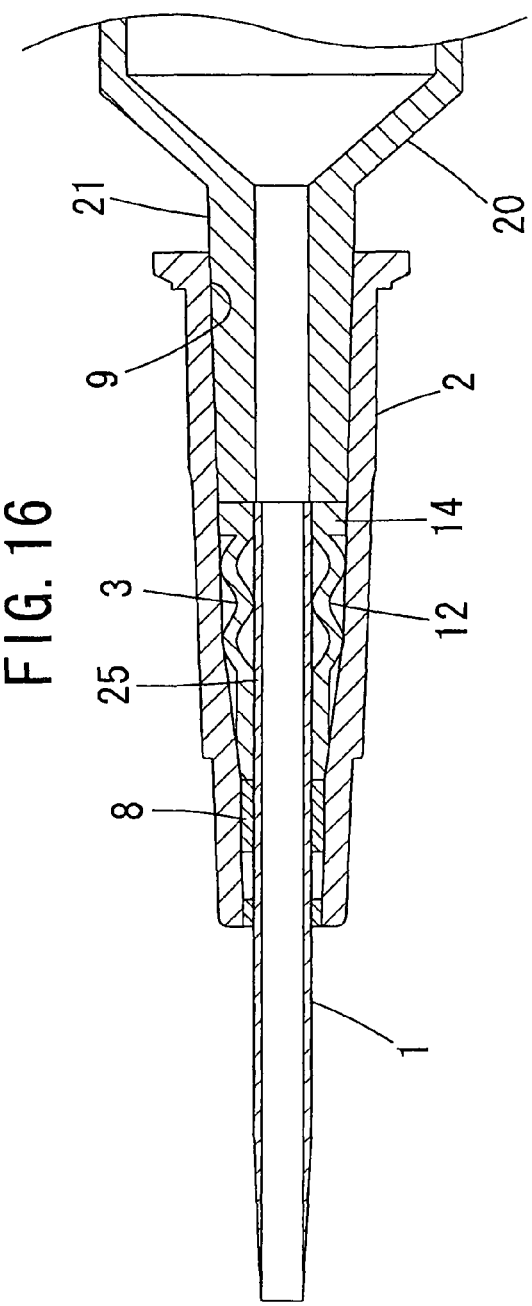
FIG. 15
FIG. 16

INDWELLING CATHETER

This application is a division of application Ser. No. 10/773,409 filed Feb. 9, 2004, now U.S. Pat. No. 7,347,839, which claims priority of Japanese patent application Nos. 2003-33635 and 2003-33636 filed Feb. 12, 2003, each of which is incorporated herein by reference.

FIELD OF THE INVENTION

The present invention relates to improvements in a connector portion of an indwelling catheter which is left implanted in an artery, a vein and the like and is used for infusion, blood transfusion, artificial dialysis and the like, and more specifically, to a catheter which is improved in a connection operation and is capable of, when left implanted in an artery, a vein and the like, preventing the leakage of blood from the catheter until a cap or a infusion line is connected to the catheter.

DESCRIPTION OF THE RELATED ART

There is heretofore been an indwelling catheter of the type which includes a female connector connected to a tube to be left implanted in an artery, a vein and the like; and a hemostasis valve which is provided in this female connector comprises a body having a slit and being fitted in the female connector and a pusher provided for slidable movement in the female connector and operative to press and open the slit of the body (refer to, for example, JP-A-2002-263197).

In the above-mentioned one, when a male connector such as a syringe is inserted into and connected to the female connector, the pusher is pressed and the slit of the body is pressed open by the pusher, whereby a fluid path is brought to an open state.

However, in the above-mentioned indwelling catheter, since a dead space is formed between the body of the hemostasis valve and the pusher within the female connector, an infusion fluid and the like substantially flow into and out of the dead space during the operation of connecting the female connector to the male connector.

Accordingly, during the connecting operation, if microorganisms enter by accident, the dead space becomes a breeding ground of various microorganisms, so that there is the risk that the dead space becomes a cause of the onset of infectious diseases.

In addition, there is also the problem that the hemostasis valve has a complicated structure made of two component parts.

BRIEF SUMMARY OF THE INVENTION

As a result of earnest investigations made by the inventors to solve the problems associated with the conventional techniques, the invention has been completed.

An object of the invention is to provide an indwelling catheter in which the structure of a hemostasis valve is simplified to reduce a dead space in a female connector and reduce the risk that the dead space becomes a cause of the onset of infectious diseases, as well as in which even if connecting operation is repeated, there is not a great risk that the function of the hemostasis valve is impaired.

The above-mentioned object and other objects of the present invention will be clarified further more in the following description, and these objects are attained by the present invention comprising the constitution mentioned below.

The invention relates to an indwelling catheter comprising:
a tube arranged in a longitudinal direction;
a female connector having a hollow form opened at its front and rear ends and being provided on a rear portion of the tube in a state of communicating with the rear portion wherein an opening taper portion tapered forwardly is formed in a longitudinal intermediate portion of an internal circumferential surface of the female connector; and
an elastically deformable hemostasis valve is provided longitudinally slidably in the opening taper portion of the female connector and an inside portion extending rearwardly from the opening taper portion,
the hemostasis valve including:
a body having a hollow form opened at its front and rear ends, the body being elastically deformed in a radially inward direction by sliding forwardly in the opening taper portion, and also being urged rearwardly by resilient force due to said elastic deformation; and
an openable/closable portion having a forwardly projecting tapered shape molded integrally with the front end of the body to close the front end opening of the body, the openable/closable portion having a front end portion to be opened in the radially outward direction by elastic deformation of the body in the radially inward direction.

The indwelling catheter may comprise:
a tube arranged in a longitudinal direction;
a female connector having a hollow form opened at its front and rear ends and being provided on a rear portion of the tube in a state of communicating with the rear portion wherein a male connector is separably connected to a rear portion of the female connector and an inner needle is removably inserted through the tube and the female connector with its front portion projecting forwardly from the tube and wherein an opening taper portion tapered forwardly is formed in a longitudinal intermediate portion of an internal circumferential surface of the female connector; and
an elastically deformable hemostasis valve pressable forwardly by the male connector is provided longitudinally slidably in the opening taper portion of the female connector and an inside portion extending rearwardly from the opening taper portion,
the hemostasis valve including;
a body having a hollow form opened at its front and rear ends, the body being elastically deformed in a radially inward direction by sliding forwardly in the opening taper portion during application of pressure by the male connector, and also being urged rearwardly by resilient force due to this elastic deformation; and
an openable/closable portion having a forwardly projecting tapered shape molded integrally with the front end of the body to close the front end opening of the body, the openable/closable portion having a front end portion to be opened by being elastically deformed in a radially outward direction during application of pressure by the inner needle and elastic deformation of the body in the radially inward direction.

The connecting taper portion, which is provided to extend successively rearwardly from the opening taper portion and to which the male connector is releasably connected, may be formed on an internal circumferential surface of the female connector and a taper ratio of the opening taper portion may be made larger than a taper ratio of the connecting taper portion.

The hemostasis valve may have a duckbill-like shape.

The indwelling catheter may comprises:
a tube arranged in a longitudinal direction;
a female connector having a hollow form opened at its front and rear ends and being provided on a rear portion of the tube in a state of communicating with the rear portion wherein a tubular connecting portion is molded integrally with the tube or the female connector, the tubular connecting portion being arranged in a longitudinal direction, communicating with the tube, being located in the female connector, and being opened at its rear end; and an elastically deformable hemostasis valve being disposed in the female connector, the hemostasis valve including:

a tubular portion fitted over the connecting portion from a rearward direction and reducible in size by forward elastic deformation; and an openable/closable portion molded integrally with a rear end of the tubular portion to close a rear end opening of the connecting portion and provided with a slit formed to extend in a radial direction, the slit being opened by being elastically deformed in a radially outward direction owing to the reduction in size of the tubular portion.

The indwelling catheter may comprises;

a tube arranged in a longitudinal direction;

a female connector having a hollow form opened at its front and rear ends and being provided on a rear portion of the tube in a state of communicating with the rear portion wherein a male connector is separably connected to a rear portion of the female connector and an inner needle is removably inserted through the tube and the female connector with its front portion projecting forwardly from the tube and wherein a tubular connecting portion is molded integrally with the tube or the female connector, the tubular connecting portion being arranged in a longitudinal direction, communicating with the tube, being located in the female connector, and being opened at its rear end; and an elastically deformable hemostasis valve pressable forwardly by the male connector is disposed in the female connector, the hemostasis valve including;

a tubular portion fitted over the connecting portion from a rearward direction and elastically deformed forwardly and reduced in size during application of pressure by the male connector; and an openable/closable portion molded integrally with a rear end of the tubular portion to close a rear end opening of the connecting portion and provided with a slit formed to extend in a radial direction, the inner needle being inserted through the slit with the slit pressed open by the inner needle, the slit being opened by elastic deformation of the openable/closable portion in a radially outward direction owing to the reduction in size of the tubular portion.

The hemostasis valve may be made of a rubber elastic material.

In the present invention, the indwelling catheter may further comprises a member having a male connector. The member may comprise an inner needle, a needle hub and a male connector or may be a syringe.

BRIEF DESCRIPTION OF THE DRAWINGS

FIGS. 1 to 9 show a first embodiment of the invention, and FIG. 1 is a cross-sectional view.

FIG. 2 is an enlarged view of an essential portion of FIG. 1.

FIG. 3 is a cross-sectional view taken along line A-A of FIG. 1.

FIG. 4 is an exploded perspective view of FIG. 1.

FIG. 5 is an enlarged view of an essential portion of FIG. 4.

FIG. 6 is a cross-sectional view taken along line B-B of FIG. 4.

FIG. 7 is a cross-sectional view showing a state in which the inner needle and the like of FIG. 1 are replaced with a syringe.

FIG. 8 is an enlarged view of an essential portion of FIG. 7.

FIG. 9 is a cross-sectional view taken along line C-C of FIG. 7.

FIGS. 10 to 16 show a second embodiment of the invention, and FIG. 10 is a cross-sectional view.

FIG. 11 is an enlarged view of an essential portion of FIG. 10.

FIG. 12 is an exploded view of FIG. 10.

FIG. 13 is an enlarged view of an essential portion of FIG. 12.

FIG. 14 is a rear view of the hemostasis valve of FIG. 13.

FIG. 15 is a cross-sectional view showing a state in which the inner needle and the like of FIG. 10 are replaced with a syringe.

FIG. 16 is an enlarged view of an essential portion of FIG. 15.

DETAILED DESCRIPTION OF THE INVENTION

Figure 1:
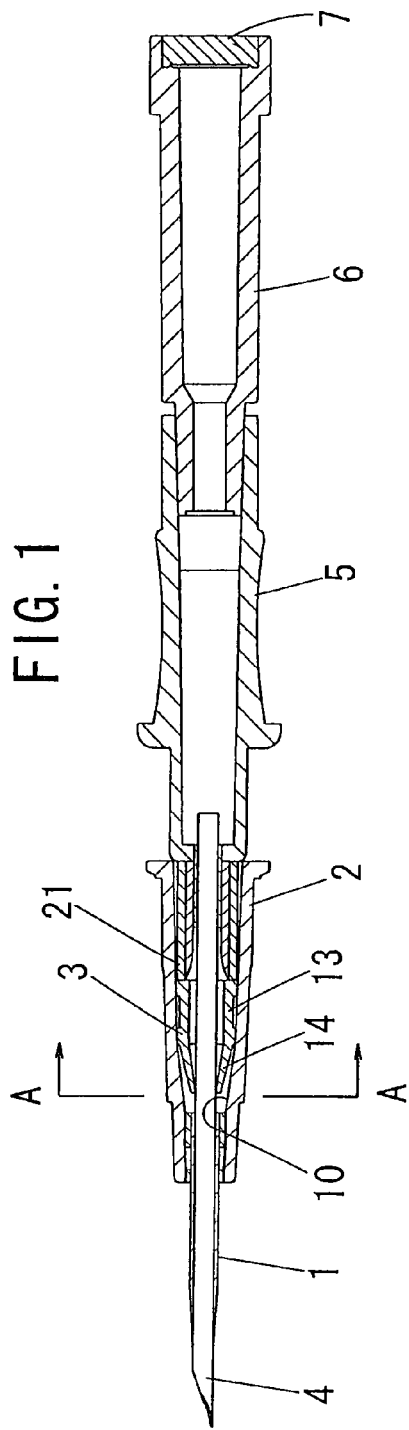

A first embodiment in which the invention is applied to an external needle type indwelling catheter will be described with reference to FIGS. 1 to 9. FIG. 1 shows a catheter, and the catheter has a tube (a catheter tube, an external needle) 1, a female connector (a catheter connector, an external needle hub) 2, a hemostasis valve 3, an inner needle (a hollow needle) 4, an inner needle hub 5, a filter cap 6, a hydrophobic filter 7, and the like.

As shown in FIGS. 2 to 9, the tube 1 is elongated and (semi)transparent and has flexibility, and is integrally molded from a plastic (resin) material and is arranged in the longitudinal direction. As this plastic material, for example, a thermoplastic resin is used. As this thermoplastic resin, various materials can preferably be enumerated, such as ethylene-tetrafluoroethylene copolymers (ETFE), tetrafluoroethylene-perfluoroalkylether copolymers (PFA), polypropylene resins, polyethylene resins, polyvinyl chloride, acrylonitrile-butadiene-styrene copolymers, polycarbonate resins, polyamide resins and polyoxymethylene resins.

The female connector 2 has a rear portion in the side of which a male connector 21 is releasably connected in the state of communicating with the inside, and has a hollow tubular form opened at its front and rear ends and is fitted on a rear portion of the tube 1 in the state of communicating with the rear portion and is fixed by an adhesive 8. The internal circumferential surface of the female connector 2 is formed into a connecting taper portion (a first taper portion) 9 located in the rear portion, an opening taper portion (a second taper portion) 10 located in a longitudinal intermediate portion, and a fixing portion 11 located in a front portion, which portions 9, 10 and 11 are successively arranged in named order toward the front. Incidentally, in FIGS. 2, 5 and 8, L1 to L3 respectively denote the lengths of the taper portions 9 and 10 and the fixing portion 11. Each of the taper portions 9 and 10 is tapered toward the front, and the taper ratio (taper angle) of the opening taper portion 10 is made larger than that of the connecting taper portion 9. A male connector 21 such as a syringe or the like is releasably connected to the inside of the connecting taper portion 9, and the tube 1 is fixed to the fixing portion 11. The female connector 2 is integrally molded from a plastic (resin) material, and as this plastic material, for example, materials similar to those of the tube 1 can be enumerated.

The hemostasis valve 3 is liquid-tightly provided for sliding movement in the longitudinal direction in the connecting taper portion 9 and the opening taper portion 10 in the female connector 2, and is elastically deformable and can be pressed toward the front by the inner needle hub 5 and the male connector. The hemostasis valve 3 has a tapered shape, for example, a duckbill-like shape (the beak of a duckbilled platypus) or a shape incorporating this shape, and the hemostasis valve 3 is made of a body (tubular portion) 13 and an openable/closable portion 14 which are integrally molded. The hemostasis valve 3 is formed of a rubber elastic material such as silicone, synthetic polyisoprene rubber, natural rubber, butyl rubber, chloroprene rubber, urethane rubber, styrene-butadiene rubber, ethylene-propylene rubber, acrylic rubber, fluororubber, or thermoplastic elastomer. Incidentally, elasticity may also be imparted to the hemostasis valve 3 by using a metallic material such as a spring steel disposed in a resin material, and a shape memory alloy, a combination of a rubber elastic material and a metallic material, or the like.

The body 13 has a hollow tubular form opened at its front and rear ends, and its front and rear portions are respectively formed as large-diameter portions 16 each having a diameter larger than the inside diameter of the rear end of the opening taper portion 10. The body 13 is located in the connecting taper portion 9 and liquid-tightly abuts on the inside surface of the connecting taper portion 9. The body 13, while being pressed by the inner needle hub 5 and the male connector 21, slides in the opening taper portion 10 toward the front and is elastically deformed in the radially inward direction, and is urged rearwardly by resilient force due to this elastic deformation.

Incidentally, in the invention, the opening taper portion 10 denotes a taper portion the rear end of which has an inside diameter smaller than the outside diameter of the body 13.

The openable/closable portion 14 has a forwardly projecting tapered shape molded integrally with the front end of the body 13, and in this example, is formed in a duckbill-like shape to openably close the front end opening of the body 13 as will be described below. Specifically, a slit 18, which extends across the entire lengthwise (diametrical) length of the front end of the openable/closable portion 14 and is located in the widthwise middle portion of the front end of the openable/closable portion 14, is formed to extend through the front end portion of the openable/closable portion 14 in the longitudinal direction, whereby the front end portion of the openable/closable portion 14 is made openable/closable. The front end portion of the openable/closable portion 14 is opened by being elastically deformed in the radial outward direction while being pressed by the inner needle 4 and when the body 13 is elastically deformed in the inward radial direction.

The inner needle 4 is removably inserted through the tube 1 and the female connector 2, and its front portion projects forwardly from the tube 1. The inner needle 4 is shaped like the elongated tube and has flexibility, and the front end is sharp-pointed. The inner needle 4 is integrally molded from, for example, stainless steel (preferably, SUS 304).

The inner needle hub 5 has a hollow tubular form opened at its front and rear ends, and its front portion is fitted over a rear portion of the inner needle 4 in the state of communicating with the rear portion and is fixed to the same by an adhesive 19, and is also removably inserted in the rear portion of the female connector 2. The inner needle hub 5 is integrally molded from a plastic (resin) material, and as this plastic material, for example, materials similar to those of the tube 1 can be enumerated.

The filter cap 6 serves to confirm flashbacks of blood and body fluids into the inner needle 4 and prevent blood and the like from leaking to the outside. The filter cap 6 has a hollow tubular form opened at its front and rear ends, and its front portion is removably inserted in a rear portion of the inner needle hub 5. The filter cap 6 is integrally molded from a (semi)transparent plastic (resin) material, and as this plastic material, for example, materials similar to those of the tube 1 can be enumerated.

The filter 7 is fitted in the rear end portion of the filter cap 6.

Figure 2:
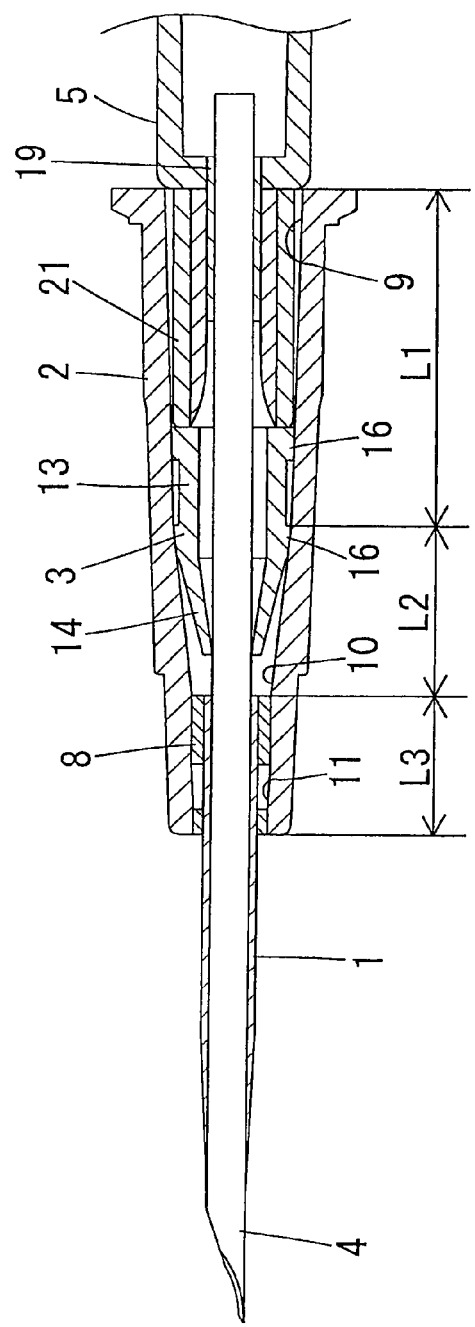
Figure 5:
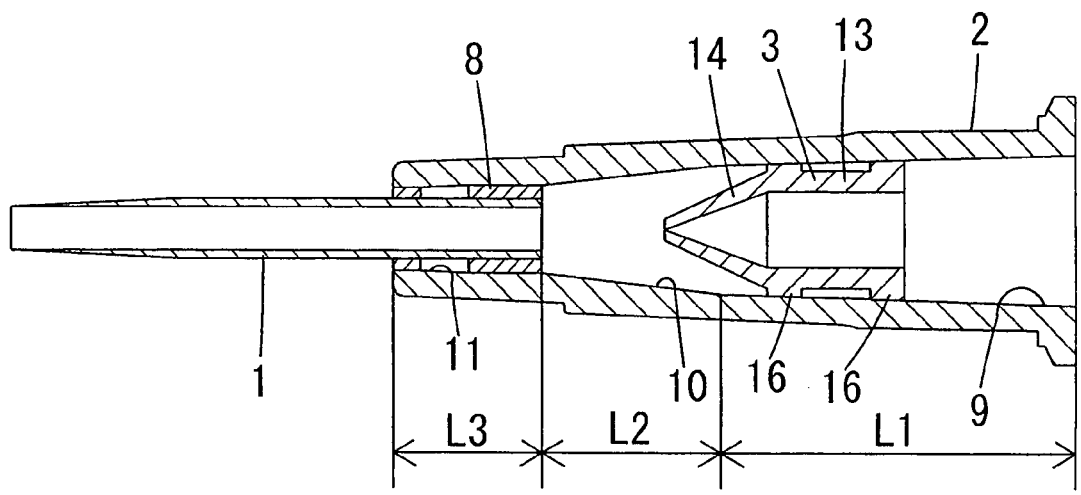
Figure 6:
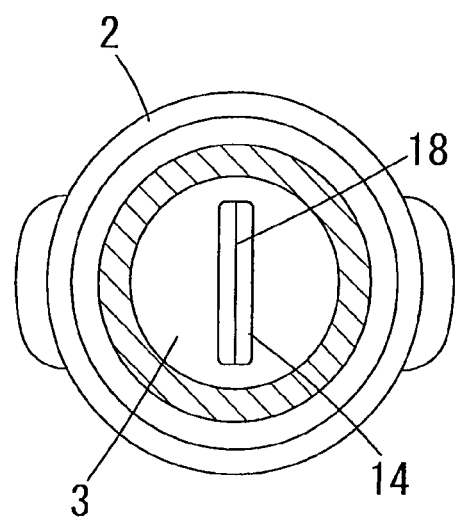

According to the above-described first embodiment, when fluid is transfused or blood is drawn from a blood vessel such as a peripheral vein in the back of a hand of a patient or from under the skin or the like of the patient, first of all, as shown in FIGS. 1 to 3, the inner needle 4 and the inner needle hub 5 of the catheter are inserted into the female connector 2 from the rear. The inner needle 4 is inserted through the tube 1 while the openable/closable portion 14 of the hemostasis valve 3 is being pressed open by the inner needle 4, and the inner needle hub 5 presses the hemostasis valve 3 toward the front to cause the body 13 of the hemostasis valve 3 to slide in the opening taper portion 10, thereby elastically deforming the body 13 in the radially inward direction. Incidentally, in this state, the body 13 is urged toward the rear by its resilient force.

Then, the inner needle 4 and the tube 1 are stuck into a blood vessel or the like of the patient. At this time, blood in the blood vessel and body fluids of the patient flash back, and flow out of the inner needle 4 into the inner needle hub 5. This outflow can be visually confirmed via the inner needle hub 5, whereby it is possible to easily confirm whether the above-described needle sticking has been correctly carried out.

In addition, during this needle sticking, the rear end opening of the inner needle hub 5 is closed by the filter cap 6 and the filter 7, whereby there is no risk that various microorganisms enters from the rear end opening of the inner needle hub 5.

After the inner needle 4 and the tube 1 have been stuck into the blood vessel or the like of the patient, the female connector 2 and the like are fixed to the back of the hand of the patient by tape or the like.

Then, the inner needle 4 and the inner needle hub 5 are extracted from the tube 1, female connector 2 and the like. Since the hemostasis valve 3 is released from the pressure of the inner needle hub 5 by this extraction, the body 13 of the hemostasis valve 3 slides toward the rear owing to its resilient force and returns to the inside of the connecting taper portion 9, and is deformed in the radially outward direction and restores to its original size, thereby closing the openable/closable portion 14 of the hemostasis valve 3. Accordingly, during/after the extraction of the inner needle 4, it is possible to prevent blood leakage and the like.

Figure 7:
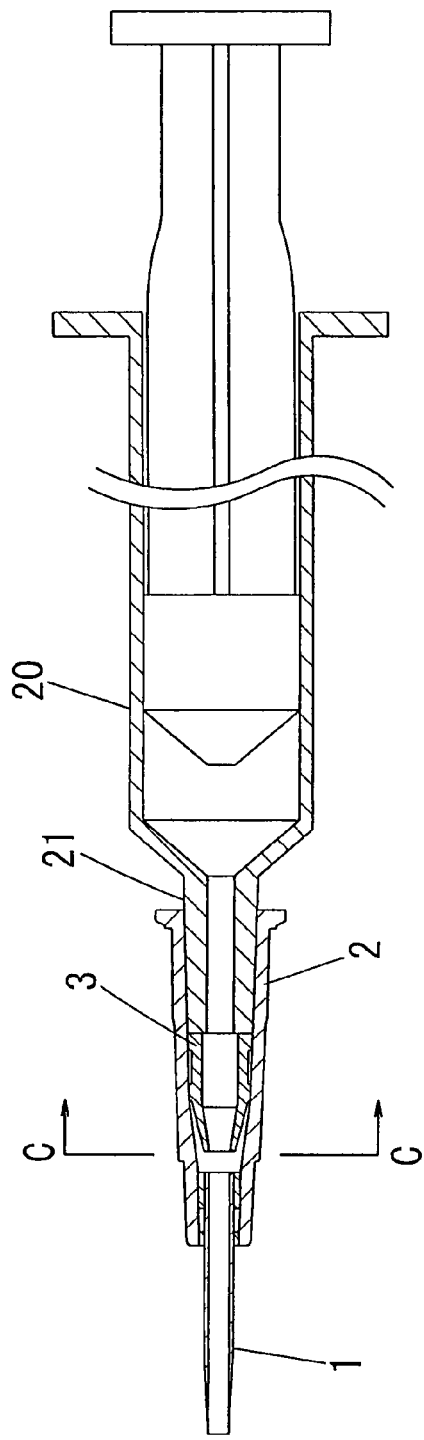
Figure 8:
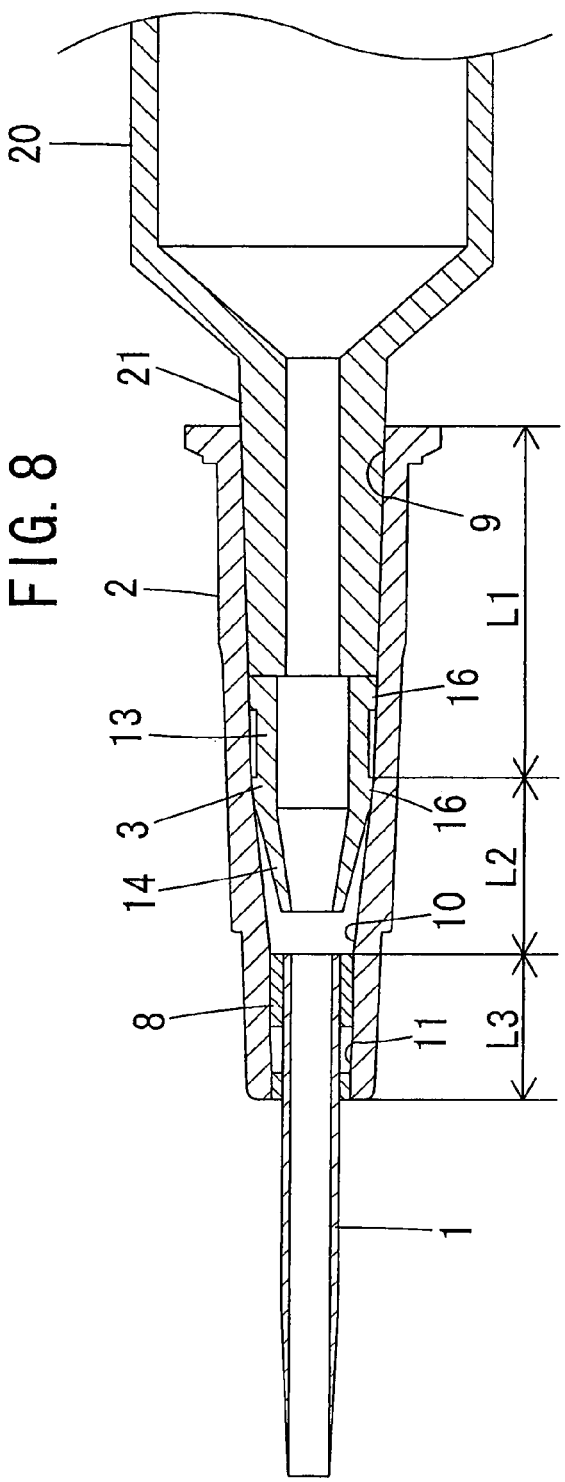
Figure 9:
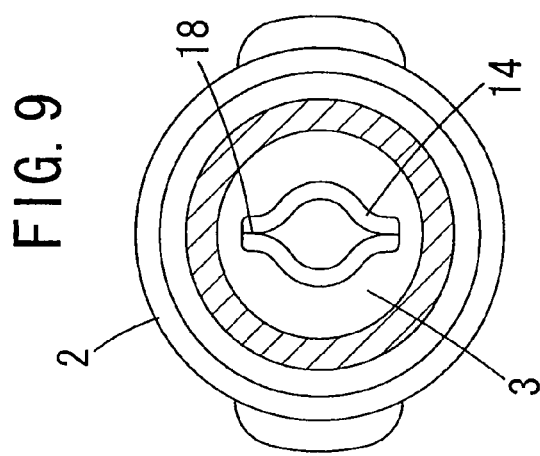

Subsequently, when infusion, drawing of blood or the like is to be started, as shown in FIGS. 7 to 9, a tip 21 of a syringe 20 illustrated as one example of a male connector is inserted into the female connector 2, and the tip (male connector) 21 is releasably taper jointed and connected to the connecting taper portion 9 of the female connector 2 and presses the hemostasis valve 3 toward the front. Accordingly, in a manner similar to the above-described one, the body 13 of the hemostasis valve 3 slides into the opening taper portion 10 and is elastically deformed in the radially inward direction, whereby the openable/closable portion 14 of the hemostasis valve 3 is opened. Then, infusion, drawing of blood or the like by the syringe 20 is started.

When infusion, collection of blood or the like is completed, the syringe 20 is extracted from the female connector 2. Since the hemostasis valve 3 is released from the pressure of the syringe 20 by this extraction, in a manner similar to the above-described one, the body 13 of the hemostasis valve 3 slides toward the rear owing to its resilient force and returns to the inside of the connecting taper portion 9, and is deformed in the radially outward direction and restores to the original size, thereby closing the openable/closable portion 14 of the hemostasis valve 3. Accordingly, during/after the extraction of the syringe 20, it is possible to prevent blood leakage and the like.

In the above-described first embodiment, since the hemostasis valve 3 is made of a single member, a dead space formed between the female connector 2 and the hemostasis valve 3 can be made small. In this manner, the dead space which is a hotbed of various microorganisms can be made small, whereby it is possible to reduce the risk that the dead space becomes a cause of the occurrence of infectious diseases.

In addition, since the hemostasis valve 3 is made of a single member, the structure is simple, and during the connection between the female connector 2 and the male connector 21, the openable/closable portion 14 of the hemostasis valve 3 is opened not by pressing open the openable/closable portion 14 of the hemostasis valve 3 by means of the male connector 21 or the like, but by sliding the hemostasis valve 3 by means of the male connector 21. Accordingly, even if connection between the female connector 2 and the male connector 21 is repeated, there is not a great risk that the function of the openable/closable portion 14, that is to say, the function of the hemostasis valve 3, is impaired.

Incidentally, although in the above-described embodiment the taper ratio of the opening taper portion and the taper ratio of the connecting taper portion are made different from each other, the taper ratios of both may be made the same.

Then, a second embodiment of the invention will be described with reference to FIGS. 10 to 16. In this description, reference will be made mainly to the difference from the above-described first embodiment. First, the connecting taper portion 9 which is tapered toward the front is formed on the internal circumferential surface of the rear portion of the female connector 2.

However, a tubular connecting portion 25 is molded integrally with the tube 1 or the female connector 2. The connecting portion 25 is arranged in the longitudinal direction, and communicates with the tube 1 and is located in the female connector 2, and is opened at its rear end. In this example, the tube 1 is extended toward the rear, and its extended portion, that is to say, a portion projecting rearwardly from the adhesive 8, is used as the connecting portion 25.

The hemostasis valve 3 is disposed forwardly of the connecting taper portion 9 of the female connector 2, and is elastically deformable. The hemostasis valve 3 is made of a tubular portion (body) 12 and the openable/closable portion 14 which are integrally molded.

The tubular portion 12 is fitted onto the connecting portion 25 from the rear, and is elastically deformed toward the front and reduced in size, by being pressed toward the front by the inner needle hub 5 and the male connector 21.

Figure 14:
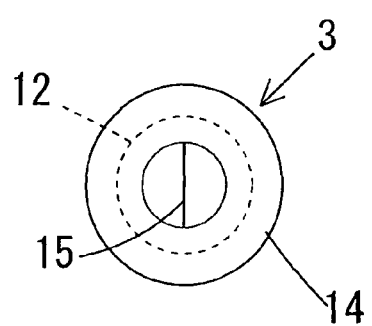

The openable/closable portion 14 is molded integrally with the rear end of the tubular portion 12 to close the rear end opening of the connecting portion 25, and as shown in FIG. 14, a slit 15, through which the inner needle is inserted with the slit 15 pressed open by the inner needle, is formed to extend in the radial direction on the middle side of the openable/closable portion 14, and the openable/closable portion 14 is elastically deformed in the radially outward direction by the reduction in size of the tubular portion 12 and by the abutment between the openable/closable portion 14 and the rear end of the connecting portion 25, whereby the slit 15 is opened and the openable/closable portion 14 is fitted over the connecting portion 25. Incidentally, the length of the slit 15 is made approximately equal to or slightly greater than the inside diameter of the tubular portion 12 and the outside diameter of the connecting portion 25.

Figure 10:
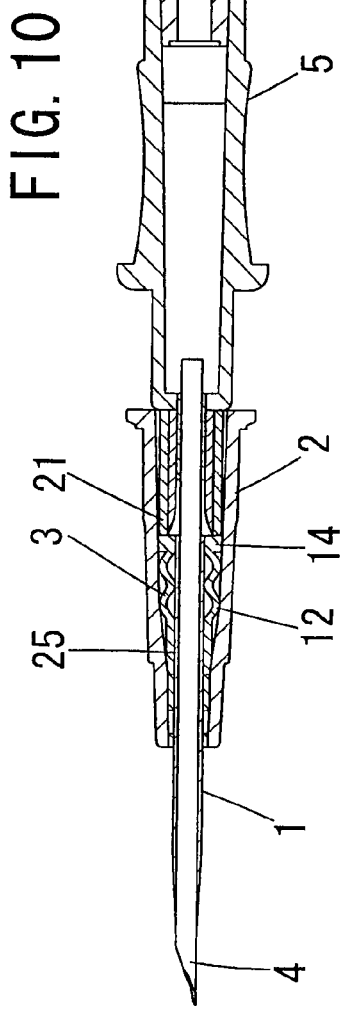
Figure 11:
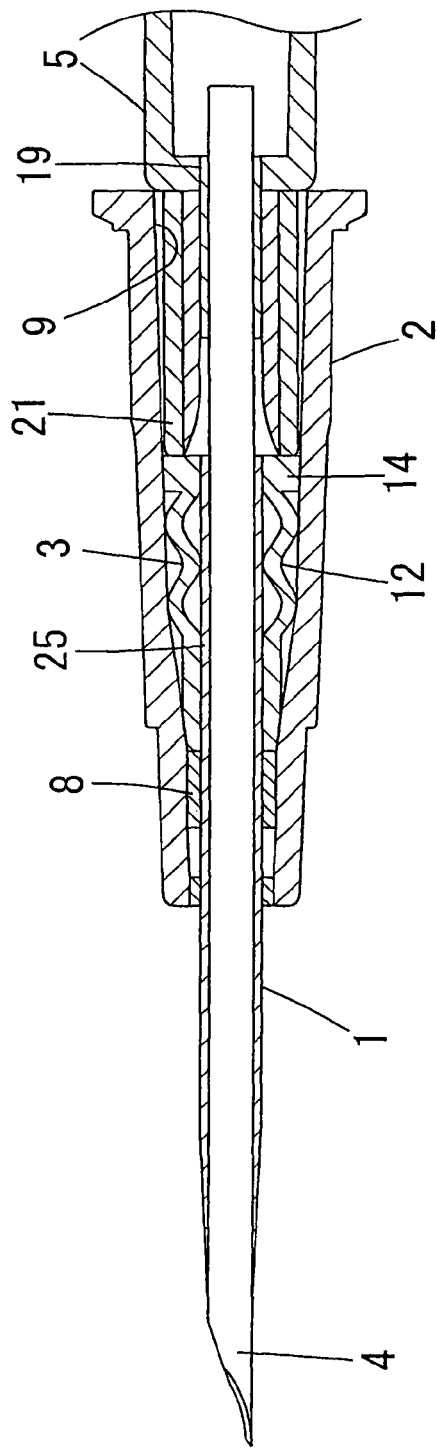
Figure 12:
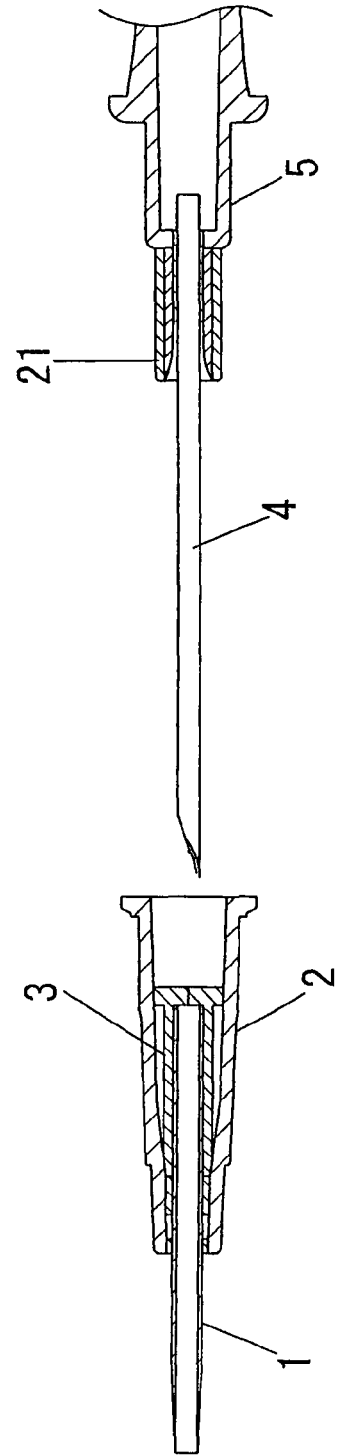
Figure 13:
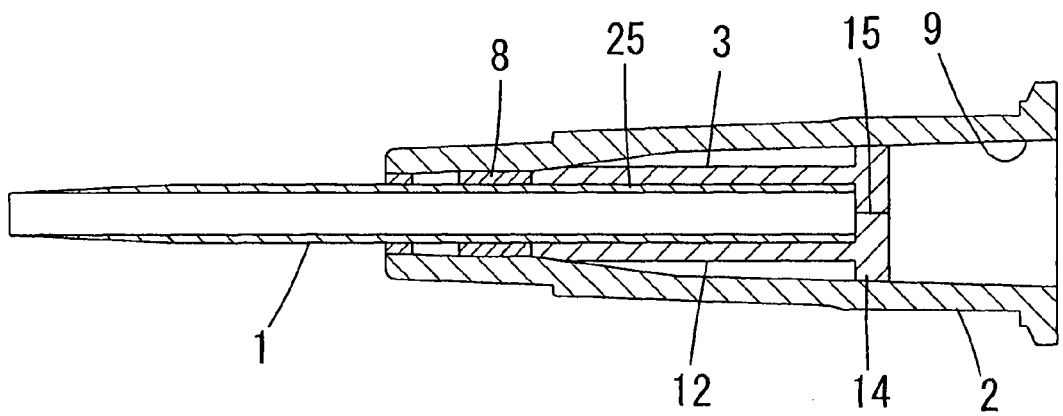

According to the above-described second embodiment, when fluid is transfused or blood is drawn from a blood vessel such as a peripheral vein in the back of a hand of a patient or from under the skin or the like of the patient, first of all, as shown in FIGS. 10 and 11, the inner needle 4 and the inner needle hub 5 of the catheter are inserted into the female connector 2 from the rear. The inner needle 4 is inserted through the tube 1 while the slit 15 of the openable/closable portion 14 of the hemostasis valve 3 is being pressed open due to elastic deformation by the inner needle 4, and the inner needle hub 5 presses the hemostasis valve 3 toward the front. Accordingly, the tubular portion 12 of the hemostasis valve 3 is elastically deformed toward the front and reduced in size, and the openable/closable portion 14 is elastically deformed to a further extent in the radially outward direction by the abutment between the openable/closable portion 14 and the rear end of the connecting portion 25, whereby the slit 15 is opened further and the openable/closable portion 14 is fitted over the connecting portion 25.

Then, in a manner similar to that described in the first embodiment, after the inner needle 4 and the tube 1 have been stuck into a blood vessel or the like of the patient, the female connector 2 and the like are fixed to the back of the hand of the patient by tape-or the like.

Then, the inner needle 4 and the inner needle hub 5 are extracted from the tube 1, the female connector 2 and the like. Since the hemostasis valve 3 is released from the pressure of the inner needle hub 5 by this extraction, the tubular portion 12 of the hemostasis valve 3 extends toward the rear owing to its resilient force and restores to its original size, thereby closing the slit 15 of the openable/closable portion 14 of the hemostasis valve 3. Accordingly, during/after the extraction of the inner needle 4, it is possible to prevent blood leakage and the like.

Subsequently, when infusion, drawing of blood or the like is to be started, as shown in FIGS. 15 and 16, the tip 21 of the syringe 20 illustrated as one example of a male connector is inserted into the female connector 2, and the tip 21 is releasably taper jointed and connected to the connecting taper portion 9 of the female connector 2 and presses the hemostasis valve 3 toward the front. Accordingly, in a manner similar to the above-described one, the tubular portion 12 of the hemostasis valve 3 is elastically deformed toward the front and is reduced in size, and the openable/closable portion 14 is elastically deformed in the radially outward direction by the reduction in size and by the abutment between the openable/closable portion 14 and the rear end of the connecting portion 25, whereby the slit 15 is opened and the openable/closable portion 14 is fitted over the connecting portion 25. Then, infusion, drawing of blood or the like by the syringe 20 is started.

When transfusion, collection of blood or the like is completed, the syringe 20 is extracted from the female connector 2. Since the hemostasis valve 3 is released from the pressure of the syringe 20 by this extraction, in a manner similar to the above-described one, the tubular portion 12 of the hemostasis valve 3 extends toward the rear owing to its resilient force and restores to the original size, thereby closing the slit 15 of the openable/closable portion 14 of the hemostasis valve 3. Accordingly, during/after the extraction of the syringe, it is possible to prevent blood leakage and the like.

What is claimed is:
1. An indwelling catheter comprising:
an outer needle arranged in a longitudinal direction;

a female connector having a hollow form opened at its front and rear ends and being provided on a rear portion of the outer needle in a state of communicating with the rear portion;

an elastically deformable hemostasis valve disposed in the female connector; and a tubular connecting means for connecting the outer needle with the hemostasis valve and being integrated with the outer needle or the female connector, the tubular connecting means being arranged in a longitudinal direction, communicating with the outer needle, being located in the female connector, and being opened at its rear end;

wherein the hemostasis valve includes:

a hemostasis valve tubular portion fitted over the tubular connecting means from a rearward direction and reducible in size by forward elastic deformation; and a hemostasis valve openable/closable portion integrated with a rear end of the hemostasis valve tubular portion to close a rear end opening of the tubular connecting means, and provided with a slit formed to extend in a radial direction, the slit being opened by being elastically deformed in a radially outward direction owing to the reduction in size of the hemostasis valve tubular portion.

2. The indwelling catheter according to claim 1, wherein a connecting taper portion which is provide to extend successively rearwardly from the opening taper portion and to which a male connector is releasably connected is formed on an inner circumferential surface of the female connector.

3. The indwelling catheter according to claim 2, wherein the hemostasis valve is pressable forwardly by the male connector.

4. The indwelling catheter according to claim 2, wherein the male connector is separably connected to a rear portion of the female connector.

5. The indwelling catheter according to claim 2, wherein the hemostasis valve tubular portion is elastically deformed forwardly and reduced in size during application of pressure by the male connector.

6. The indwelling catheter according to claim 1, wherein an inner needle is removably inserted through the outer needle.

7. The indwelling catheter according to claim 6, wherein the inner needle is removably inserted through the outer needle and the female connector with its front portion projecting forwardly from the outer needle.

8. The indwelling catheter according to claim 6, wherein the inner needle is inserted through the slit.

9. The indwelling catheter according to claim 1, wherein the hemostasis valve is made of a rubber elastic material.

10. The indwelling catheter according to claim 1 further comprising a connecting member.

11. The indwelling catheter according to claim 10 wherein the connecting member comprises an inner needle, a needle hub and a male connector.

12. The indwelling catheter according to claim 11 wherein the connecting member having the male connector is a syringe.

* * * * *